United States Patent [19]

Ramsden et al.

[11] Patent Number: 4,650,784
[45] Date of Patent: Mar. 17, 1987

[54] BONDED PHASE OF SILICA FOR SOLID PHASE EXTRACTION

[75] Inventors: Hugh E. Ramsden, Scotch Plains, N.J.; Joseph M. Patterson, III, New Britain, Pa.

[73] Assignee: J. T. Baker Chemical Company, Phillipsburg, N.J.

[21] Appl. No.: 831,333

[22] Filed: Feb. 20, 1986

[51] Int. Cl.$^4$ .................... B01J 20/10; B01J 20/22
[52] U.S. Cl. .................... 502/407; 502/401; 210/198.2; 210/502; 55/67; 55/386
[58] Field of Search ............... 502/401, 402, 407, 400; 210/198.2, 502; 55/67, 386

[56] References Cited

U.S. PATENT DOCUMENTS

| | | | |
|---|---|---|---|
| 3,960,521 | 6/1976 | Kruppa et al. | 502/401 |
| 3,987,058 | 10/1976 | Saunders et al. | 502/401 |
| 4,242,227 | 12/1980 | Nestrick et al. | 502/401 |
| 4,324,681 | 4/1982 | House | 502/401 |
| 4,329,254 | 5/1982 | Chmielowiec | 502/401 |
| 4,512,898 | 4/1985 | Oi et al. | 502/407 |
| 4,522,724 | 6/1985 | Ramsden | 502/402 |
| 4,523,997 | 6/1985 | Crane et al. | 502/402 |
| 4,540,486 | 9/1985 | Ramsden | 502/402 |
| 4,551,245 | 11/1985 | Ramsden et al. | 502/401 |

OTHER PUBLICATIONS

M. Elsohly et al., Analysis of the Major Metabolite of Δ$^9$-Tetrahydrocannabinol in Urine, Journal of Analytical Toxicology, vol. 7, Nov./Dec. 1983, pp. 262–264.
D. Black et al., Urine Cannabinoid Analysis: An Integrated Multi-Method Approach, Journal of Analytical Toxicology, vol. 8, Sep./Oct. 1984, pp. 224–227.

Primary Examiner—John Doll
Assistant Examiner—Anthony McFarlane
Attorney, Agent, or Firm—George W. Rauchfuss, Jr.

[57] ABSTRACT

A bonded phase silica product of the formula:

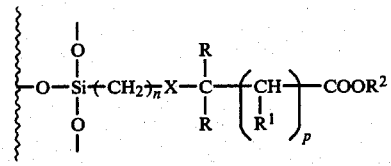

in which

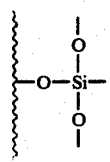

is the backbone of a silica gel or controlled pore glass, X is selected from —O—, —S—,

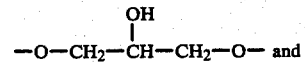 and

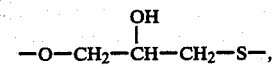

, each R and R$^1$ are each independently selected from hydrogen, an alkyl group of from 1 to 3 carbon atoms and —CH$_2$)$_m$COOR$^3$, R$^2$ and R$^3$ are each independently alkyl of from 1 to 4 carbon atoms, n is an integer of from 2 to 5, p is zero or one and m is an integer of from 1 to 4, is suitable for use in solid phase extraction for cleanup of urine samples for analysis of cannabinoids.

30 Claims, No Drawings

BONDED PHASE OF SILICA FOR SOLID PHASE EXTRACTION

FIELD OF THE INVENTION

This invention relates to solid phase extraction material especially such material useful for the cleanup of urine samples for analysis of cannabinoids in urine.

BACKGROUND TO THE INVENTION

Detection of marihuana use through analysis of biological samples, such as urine or blood, is coming into more widespread use. Because use of urine samples involves a non-invasive and more convenient process, detection of metabolites of Δ-9-tetrahydrocannabinol in urine has begun to find greater popularity. Additionally, the use of such assay procedure has begun to develop greater importance and more widespread use not only because of its use to initially detect marihuana users but as an adjunct of drug counseling programs as a screening procedure to monitor compliance with withdrawal procedures and continued abstinence from marihuana use.

Of the several metabolites of Δ-9-tetrahydrocannabinol found in urine the major is 11-nor-Δ-9-tetrahydrocannabinol-9-carboxylic acid, hereinafter referred to as THC-COOH, in either its free or conjugated (glucuronide) form. Various non-automated processes exist for detection of THC-COOH in urine, such as thin layer chromatography, gas chromatography, gas chromatography/mass spectrometry, radioimmunoassay, enzyme multiplied immunoassay and more recently high performance liquid chromatography (HPLC). However, such processes are quite labor intensive and due to the numerous and varied interferents in the urine sample are quite cumbersome to carry out. Additionally, it is difficult to measure THC-COOH in urine because of the complex nature of this matrix. The extraction of THC-COOH from urine is rendered more difficult because THC-COOH is one organic acid among a large number and variety of organic acids present in urine. A number of these organic acids have chromatographic properties which are similar to THC-COOH and will interfere with its measurement. Therefore, in order to be able to obtain a meaningful and relatively quick measurement of THC-COOH in urine one must be able to selectively extract it from the urine sample.

Current techniques for screening total urine samples for the presence of THC-COOH are generally either by thin layer chromatography or the Enzyme Multiplied Immunoassay Technique (EMIT) of Syva Company. Once a positive sample is detected a confirmational analysis is performed, usually by gas chromatography/mass spectrometry. However, with adequate cleanup of the urine sample, that is concentration of THC-COOH in the urine sample, and the use of an internal standard, confirmation by HPLC is possible. Thus, a great need exists for a much more satisfactory method of cleanup of urine samples to concentrate THC-COOH present in said samples. A bonded phase chromatographic packing that uniquely and specifically extracts THC-COOH from human urine would be highly desirable. Moreover, a bonded phase that is specific enough for THC-COOH yet permits selective elution of THC-COOH from the column without removing the impurities from the column or selective elution of the impurities from the column without removing the THC-COOH would be most desirable. A bonded phase that provides a purified urine extract clean enough to permit a more sensitive analysis of THC-COOH by confirmational methods, such as by HPLC, is greatly needed. Impure extracts also result in high and noisy baselines that decrease the capability for detecting low levels of THC-COOH. Cleanup of urine samples sufficient to detect low levels of THC-COOH would be most desirable.

BRIEF DESCRIPTION OF THE INVENTION

In accordance with the invention, a bonded phase permitting the extraction of a more highly purified or concentrated form of THC-COOH from human urine is provided by a bonded phase silica product of the formula:

(Formula I)

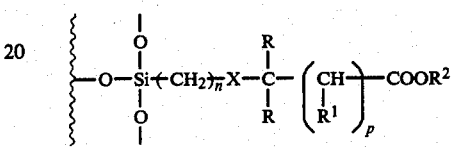

in which

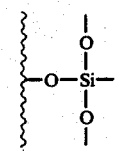

is the backbone of a silica gel or controlled pore glass, X is selected from —O—, —S—,

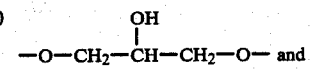 and

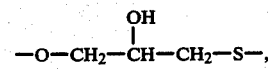, each R and $R^1$ are each independently selected from hydrogen, an alkyl group of from 1 to 3 carbon atoms and —(CH$_2$)$_m$COOR$^3$, $R^2$ and $R^3$ are each independently alkyl of from 1 to 4 carbon atoms, n is an integer of from 2 to 5, p is zero or one and m is an integer of from 1 to 4. With such bonded phase silica products one obtains a much purer extract of THC-COOH from urine than from previously used or available bonded phases and this permits quantitation at much lower levels of THC-COOH and also more accurate measurement of THC-COOH. Additionally using this bonded phase a much simpler and more rapid extraction of THC-COOH is obtained.

DETAILED DESCRIPTION OF THE INVENTION

The bonded phase silica products of Formula I of this invention are prepared by reacting in a suitable inert organic solvent, and where required, in the presence of a free radical initiator as a catalyst:

(a) a bonded phase silica reactant of the formula:

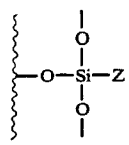
(Formula II)

wherein

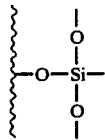

is as defined in Formula I and Z is selected from

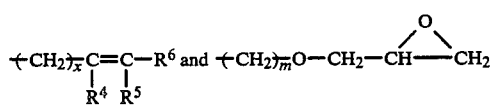

wherein $R^4$, $R^5$ and $R^6$ are each independently selected from hydrogen and alkyl of 1 to 3 carbon atoms and x is an integer of from zero to 3 with the proviso that the total number of carbon atoms in the radical Z, and Z is the unsaturated group, does not exceed 5 carbon atoms, and m is an integer of from 2 to 5, with (b) a compound of the formula:

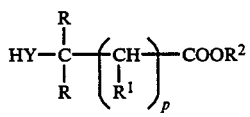
(Formula III)

wherein Y is selected from —O— and —S— and R, $R^1$, $R^2$ and p are as defined in Formula I.

The bonded phase silica reactants of Formula II are preferably those based on silica gel or controlled pore glass (CPG). The silica gel is silica gel having an average particle diameter of from about 3 to about 70 microns and an average pore size of from about 50 to about 1000, preferably about 50 to about 250 Angstrom units. The particulate controlled pore glass, which is a silicate support material similar to silica for use in liquid chromatography is commercially available, for example from the Pierce Chemical Co., of Rockford, Ill., is CPG having an average particle diameter of from about 37 to about 177 microns and an average pore size of from about 40 to about 1000 Angstrom units, preferably of about 40 to about 500 Angstroms.

The silica bonded phase products of Formula I of this invention are generally prepared in accordance with the following steps:

A. reacting a silica bonded phase of Formula II, as set forth hereinbefore, wherein the silica backbone is either particulate silica gel having an average particle diameter of from about 3 to about 70 microns and an average pore size of from about 50 to about 1000 Angstrom units, or particulate controlled pore glass having an average particle diameter of from about 37 to 177 microns and an average pore size of from about 40 to about 1000 Angstroms, in an inert organic solvent having a boiling point of at least about 80° C. and inert to free radicals, a free radical initiator where required, with a compound of Formula III, as set forth hereinbefore, said reaction being conducted at ambient to about 80° C. or more for about 2 to about 10 hours;

B. recovering the resultant solid fraction from the reaction mixture; and

C. heating said solid fraction at a temperature and for a time sufficient to dry the product.

Among the inert organic solvents suitable for preparing the bonded phase silica products of Formula I are aliphatic hydrocarbons such as, for example, heptane, octane, nonane and the like; aromatic hydrocarbons such as, for example, benzene, toluene, xylene and the like; and such other inert solvents as glyme, diglyme and the like. In general a 1:5 ratio of bonded phase silica reactant of Formula II in grams to organic solvent in milliliters affords a suitable reaction mixture.

When the bonded phase silica reactant of Formula II is a reactant in which Z is the group

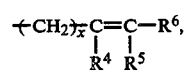

a free radical initiating catalytic amount of a free radical initiator is employed as a catalyst. Such free radical initiators are known in the art, such as for example, organic peroxides, such as benzoyl peroxide, or azobisisobutyronitrile and the like.

As examples of the bonded phase silica reactants of Formula II employed in the reaction of this invention there may be mentioned, for example, glycidoxypropyl bonded phase silica of the formula

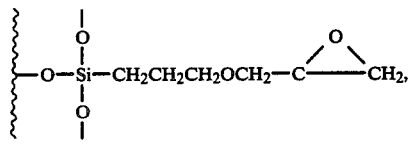

and allyl bonded phase silica of the formula

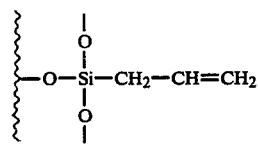

and the like.

As examples of the reactants of Formula III employed as reactants in the reaction of this invention there may be mentioned, for example, dimethyl tartrate, dimethyl maleate, methyl lactate, methyl 2-hydroxyisobutyrate, ethyl mercaptoacetate, methyl 3-mercaptopropionate, dimethyl mercaptosuccinate, trimethyl citrate, 2-mercapto dimethylsuccinate, 2-mercaptomethyl dimethylsuccinate, 2-mercapto ethyl butyrate, 2-mercapto ethylpropionate, 2-mercapto butylpropionate, trimethyl citrate and the like.

In general, the reactants of Formulas II and III are reacted in stoichiometric equivalent amounts or with a slight excess of the reactant of Formula III. The reaction may be conducted at ambient temperature although elevated temperatures of about 80° C. or more may be utilized to enhance the rate of reaction. The reaction proceeds readily to substantial completion (Step 1) within about 2-10 hours. Stirring during admixture of the reactants is advantageously employed although the reaction thereafter may continue without further stirring.

The resultant solid fraction is recovered from the reaction mixture by conventional physical means, for example, filtration, centrifugation and the like. In general, a filtering means sufficient to retain a particle size of 5 microns is suitable whereas centrifuging is suitable for a particle size of 3 microns.

The recovered solid fraction is then heat cured at a temperature and for a time sufficient to dry. In general, from about 1-4 hours at about 40°-120° C. has been found sufficient.

It is also possible to prepared the bonded phase silica products of Formula I of this invention where X is —S— by reacting, in the presence of a free radical initiator and a suitable organic solvent, as previously discussed, a mercaptoalkyl bonded phase silica of the formula (Formula IV)

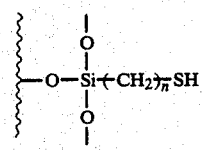

wherein n is an integer of from 2 to 5, and preferably 3, with a compound of the formula (Formula V)

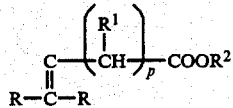

wherein each R, $R^1$ and $R^2$ and p are as defined in Formula I. The suitable reaction conditions of time, temperature and purification methods are generally the same as set forth hereinbefore with respect to the reaction of compounds of Formulas II and III.

The bonded phase reaction products of Formula I constitute new and useful bonded phases for the purification, concentration and separation of THC-COOH, especially from human urine, and are particularly suitable for use with solid phase extraction instrumentation especially in high performance liquid chromatography (HPLC) applications. The novel bonded phase product may be employed as column packing and be of various mesh sizes, for example, from about 50 to about 600 mesh. An example of the methodology suitable for purification and concentration or separation of THC-COOH is similar to that reported in the literature using other but much less effective and less efficient bonded phases, for example, the methodology disclosed by M. Elsohly, *J. Analytical Toxicology*, Vol. 7, pp. 262-264, November/December 1983.

In the following examples the bonded phase silica of Formula II employed as reactants, namely glycidoxypropyl bonded phase silica, allyl bonded phase silica and mercaptopropyl bonded phase silica were prepared in the following exemplary manner.

PREPARATION A

Glycidoxypropyl Bonded Phase Silica Gel

To 100 g silica gel, 40μ, 60 Å, is added 40 ml glycidoxypropyltrimethoxy silane in 500 ml toluene and 8 ml water with stirring. The reaction mixture is permitted to stand at ambient temperature overnight and the solid reaction product is filtered, washed twice with toluene and twice with methanol. The reaction product is placed in an 80° C. oven for about 3 hours to cure and dry the product. Yield: 115.1 g; Analysis 6.10% C, 1.57% H.

PREPARATION B

Mercaptopropyl Bonded Phase Silica Gel

To 100 g silica gel, 40μ, 60 Å, is added 112.5 g mercaptopropyltrimethoxysilane in 1250 ml toluene and 20 ml water with stirring. After standing overnight at ambient temperature the solid reaction product is filtered and washed twice with toluene and twice with methanol. The reaction product is placed in an 80° C. oven for about 3½ hours to cure and dry the product. Yield: 304.2 g; Analysis 3.73% C, 1.17% H, 3.14% S.

PREPARATION C

Allyl Bonded Phase Silica Gel

To 100 g silica gel, 40μ, 60 Å, is added 40 ml allyltrimethoxysilane in 500 ml toluene and 1 ml water with stirring. After standing overnight at ambient temperature the reaction product is filtered, washed twice with toluene and twice with methanol. The reaction product is placed in an 80° C. oven for about 5½ hours to cure and dry the product. Yield: 110.2 g; Analysis 3.88% C, 1.24% H.

Exemplary of the preparation of the new bonded phases products according to the invention are the following representative examples.

EXAMPLE 1

To 50 ml toluene is added 10 g mercaptopropyl bonded phase silica, 4 ml dimethyl maleate and 0.25 g benzoyl peroxide with stirring. The reaction mixture is placed in a water bath maintained at about 80° C. for about 4½ to 5 hours. The reaction mixture is filtered and the filter cake washed twice with toluene and twice with methanol and dried in an oven at about 80° C. for a period of about 1 to 1½ hour. Yield: 10.24 g; Analysis 6.59% C, 1.55% H, 3.20% S.

EXAMPLE 2

In the method of Example 1, 4 ml dimethyl itaconate is employed in place of dimethyl maleate. Yield: 10.56 g; Analysis 7.94% C, 1.78% H, 2.27% S.

EXAMPLE 3

In the method of Example 1, 4 ml ethyl crotonate is employed in place of dimethyl maleate. Yield: 10.08 g; Analysis 5.70% C, 1.62% H, 3.12% S.

EXAMPLE 4

In the method of Example 1, 4 ml butyl acrylate is employed in place of dimethyl maleate, the water bath is maintained at about 75° C. and 0.05 g azobisisobutyronitrite employed in place of benzoyl peroxide. Yield: 11.1 g; Analysis 10.86% C, 2.29% H, 3.21% S.

EXAMPLE 5

To 50 ml toluene is added 10 g allyl bonded phase silica, 4 ml ethyl mercaptoacetate and 0.05 g azobisisobutyronitrite with stirring. The reaction mixture is placed in a water bath maintained at about 75° C. for about 5 hours. The reaction mixture is filtered and the filter cake washed twice with toluene and twice with methanol and dried in an oven at about 80° C. for about 105 minutes. Yield: 11.15 g; Analysis 7.03% C, 1.55% H, 2.55% S.

EXAMPLE 6

In the method of Example 5, 4 ml methyl mercaptopropionate is employed in place of ethyl mercaptoacetate. Yield: 11.23 g; Analysis 6.95% C, 1.58% H, 2.70% S.

EXAMPLE 7

In the method of Example 5, 4 ml dimethyl mercaptosuccinate is employed in place of ethyl mercaptoacetate. Yield: 11.50 g; Analysis 7.48% C, 1.52% H, 2.68% S.

EXAMPLE 8

To 50 ml toluene is added 10 g glycidoxypropyl bonded phase silica, 4 ml methyl mercaptoacetate and 0.5 ml water with stirring. The reaction mixture is placed in a water bath maintained at about 80° C. for about 4 hours. The reaction mixture is filtered, washed twice with toluene and twice with methanol and dried in an oven at about 80° C. for about 1 hour. Yield: 10.5 g; Analysis 7.14% C, 1.54% H, 1.55% S.

EXAMPLE 9

In the method of Example 8, 4 ml methyl mercaptopropionate is employed in place of methyl mercaptoacetate. Yield: 10.4 g; Analysis 6.73% C, 1.41% H, 1.14% S.

EXAMPLE 10

To 50 ml toluene is added 10 g glycidoxypropyl bonded phase silica, 4 trimethyl citrate and 250 μl 1N HCl with stirring. The reaction mixture is placed in a water bath maintained at about 80° C. for about 5 hours. The reaction product is filtered and the filter cake washed twice with toluene and twice with methanol and dried in an oven at about 80° C. for about 1 hour. Yield: 10.05 g; Analysis 7.57% C, 1.63% H.

EXAMPLE 11

In the method of Example 10, 4 ml dimethyl malate is employed in place of trimethyl citrate. Yield: 10.53 g; Analysis 7.64% C, 1.49% H.

EXAMPLE 12

In the method of Example 11, 4 ml dimethyl mercaptosuccinate is employed in place of trimethyl citrate and 250 μl water in place of 1N HCl. Yield: 10.57 g; Analysis 6.77% C, 1.53% H, 1.03% S.

EXAMPLE 13

In the method of Example 11, 4 ml dimethyl tartrate is employed in place of trimethyl citrate. Yield: 10.42 g; Analysis 6.14% C, 1.25% H.

EXAMPLE 14

In the method of Example 11, 4 ml methyl lactate is employed in place of trimethyl citrate. Yield: 10.32 g.

As exemplary of the use of the bonded phase products of this invention in the cleanup of urine samples for analysis of cannabinoids reference may be had to the following Example. In the following Example the urine sample is first hydrolized to hydrolyze the conjugated form of THC-COOH to free form for chromatographic processing according to this invention. Typically such hydrolysis of a urine sample is conducted in the following manner. Three ml of urine, 3 ml of distilled water and 300 microliters of 10N KOH solution are added to a 15 ml screw top tube. The tube is capped and the solution mixed thoroughly and the tube placed in a 60° C. water bath for about 20 minutes. Following this hydrolysis step the ph of the hydrolysate is adjusted to a ph of 6 with the addition of the appropriate amount of concentrated HCL.

EXAMPLE 15

A standard 3 ml polypropylene solid phase extraction column cartridge (serological grade) is dry packed with 500 mg of the bonded phase from Example 1. The bottom of this cartridge is then friction fitted via Leur type fitting onto a suitable vacuum manifold. The vacuum is then increased to 14 inches of mercury which results in a flow rate of 5 ml/minute. The column is then conditioned to wet the bonded phase and to rinse out solubles by adding two 2 ml aliquots of methanol following by two 2 ml aliquots of distilled water (care being taken not to let the column run dry during or following conditioning). The vacuum is then turned off. Enough distilled water to fill the cartridge ⅔ of the way is then introduced. A 15 milliliter standard polypropylene (serological grade) reservoir is then friction fitted to the top of the extract column via an adaptor. Five ml of distilled water is then introduced into the column along with the hydrolized urine sample. This entire solution is then aspirated through the column at a flow rate of 5 ml/minute (14 inches of mercury). The reservoir is rinsed with a small portion of distilled water after it has run dry. The extraction column is allowed to run dry and then the reservoir and the adaptor are removed. At this point one observes a colored zone of about 2 millimeters at the top of the cartridge. This zone consists of the extracted THC-COOH as well as a large amount of co-extracted impurities. These impurities are washed from the bonded phase by aspirating through the column at a flow rate of 5 ml/minute two one ml aliquots of 45% acetonitrile/55% 0.1N HCL in water solution. The colored zone at the top of the column is displaced from the column by the first aliquot of the wash solution. The column is allowed to air dry for one minute before the vacuum is turned off. Next, a rack containing a 3 ml glass sample collection tube is placed in the vacuum manifold in such a way that the eluant from the solid phase extraction column is collected. The vacuum is again adjusted so that a flow rate of 5 ml/minute is obtained (14 inches mercury) and three 0.5 ml aliquots of 100% acetonitrile is introduced to the column. Once the column has dried the vacuum is turned off and the sample collection tube containing the concentrated THC-COOH sample eluant is removed from the rack in the vacuum manifold.

The bonded phases of this invention provide a much faster, easier and more efficient sample preparation technique, that is concentration of THC-COOH in the sample, than is possible with heretofore available bonded phases.

What is claimed is:

1. A solid phase bonded silica product of the formula:

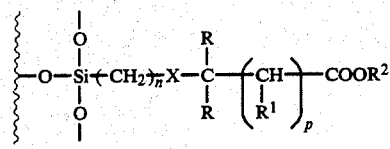

in which

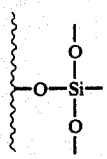

is the backbone of a silica gel or controlled pore glass, X is selected from the group consisting of —O—,—S—,

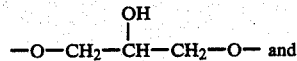

$$-O-CH_2-CH(OH)-CH_2-S-,$$

each R and $R^1$ are each independently selected from the group consisting of hydrogen, an alkyl group of from 1 to 3 carbon atoms and $-CH_2)_mCOOR^3$, $R^2$ and $R^3$ are each independently an alkyl group of from 1 to 4 carbon atoms, n is an integer of from 2 to 5, p is zero or one and m is an integer of from 1 to 4.

2. A solid phase bonded silica product of claim 1 wherein the silica is selected from the group consisting of particulate silica gel having an average particle diameter of from about 3 to about 70 microns and an average pore size of from about 50 to about 1000 Angstrom units, and particulate controlled pore glass having an average particle diameter of from about 37 to about 177 microns and an average pore size of from about 40 to about 1000 Angstrom units.

3. A solid phase bonded silica product of claim 2 wherein the silica is particulate silica gel having an average particle diameter of from about 3 to about 70 microns and an average pore size of from about 50 to about 1000 Angstrom units.

4. The solid phase bonded silica product of claim 2 wherein n is 3, X is —S—, each R is selected from hydrogen, —CH$_3$ or —CH$_2)_m$COOR$^3$ where m is 1 and R$^3$ is —CH$_3$, p is zero or 1, R$^1$ is hydrogen or —CH$_2)_m$COOR$^3$ where m is 1 and R$^3$ is —CH$_3$, and R$^2$ is selected from —CH$_3$, —C$_2$H$_5$ and —C$_4$H$_9$.

5. The solid phase bonded silica product of claim 2 in which n is 3, X is

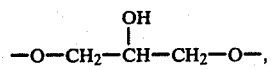

each R is H, p is zero and $R^2$ is —CH$_3$.

6. The solid phase bonded silica product of claim 2 in which n is 3, X is —S—, each R is hydrogen, p is zero and $R^2$ is —C$_2$H$_5$.

7. The solid phase bonded silica product of claim 2 in which n is 3, X is —S—, each R is hydrogen, p is 1, $R^1$ is hydrogen and $R^2$ is —CH$_3$.

8. The solid phase bonded silica product of claim 2 in which n is 3, X is —S—, each R is hydrogen, p is zero and $R^2$ is —C$_2$H$_5$.

9. The solid phase bonded silica product of claim 2 in which n is 3, X is —S—, one R is hydrogen and the other R is —CH$_2)_m$COOR$^3$ where m is 1 and R$^3$ is —CH$_3$, p is zero and $R^2$ is —CH$_3$.

10. The solid phase bonded silica product of claim 2 in which n is 3, X is —O—, one R is hydrogen and the other R is —CH$_3$, p is zero and $R^2$ is —CH$_3$.

11. The solid phase bonded silica product of claim 2 in which n is 3, X is —O—, each R is —CH$_2)_m$COOR$^3$ where m is 1 and R$^3$ is —CH$_3$, p is zero and $R^2$ is —CH$_3$.

12. The solid phase bonded silica product of claim 2 in which n is 3, X is —S—, each R is hydrogen, p is 1, $R^1$ is —CH$_2)_m$COOR$^3$ where m is 1 and R$^3$ is —CH$_3$, and $R^2$ is —CH$_3$.

13. The solid phase bonded silica product of claim 2 in which n is 3, X is —S—, each R is hydrogen, p is 1, $R^1$ is hydrogen and $R^2$ is —C$_4$H$_9$.

14. A column suitable for solid phase extraction comprising a column packed with a solid phase bonded silica product of the formula:

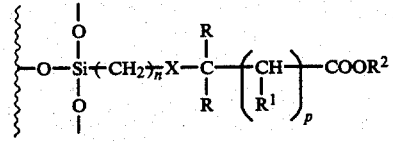

in which

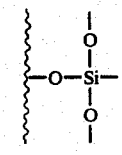

is the backbone of a silica gel or controlled pore glass, X is selected from the group consisting of —O—, —S—,

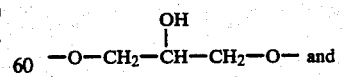

$$-O-CH_2-CH(OH)-CH_2-S-,$$

each R and $R^1$ are each independently selected from the group consisting of hydrogen, an alkyl group of from 1 to 3 carbon atoms and $-CH_2)_mCOOR^3$, $R^2$ and $R^3$ are each independently an alkyl group of from 1 to 4 carbon atoms, n is an integer of from 2 to 5, p is zero or one and m is an integer of from 1 to 4.

15. A column of claim 14 wherein the silica is selected from the group consisting of particulate silica gel having an average particle diameter of from about 3 to about 70 microns and an average pore size of from about 50 to about 1000 Angstrom units, and particulate controlled pore glass having an average particle diameter of from about 37 to about 177 microns and an average pore size of from about 40 to about 1000 Angstrom units.

16. A column of claim 15 wherein the silica is particulate silica gel having an average particle diameter of from about 3 to about 70 microns and an average pore size of from about 50 to about 1000 Angstrom units.

17. A column of claim 15 wherein in the solid phase bonded silica product n is 3, X is —S—, each R is selected from hydrogen, —CH$_3$ or —CH$_2$)$_m$COOR$^3$ where m is 1 and R$^3$ is —CH$_3$, p is zero or 1, R$^1$ is hydrogen or —CH$_2$)$_m$COOR$^3$ where m is 1 and R$^3$ is —CH$_3$, and R$^2$ is selected from —CH$_3$, —C$_2$H$_5$ and —C$_4$H$_9$.

18. A column of claim 15 wherein in the solid phase bonded silica product n is 3, X is

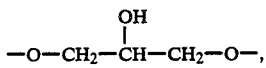

each R is H, p is zero and R$^2$ is —CH$_3$.

19. A column of claim 15 wherein in the solid phase bonded silica product n is 3, n is —S—, each R is hydrogen, p is zero and R$^2$ is —C$_2$H$_5$.

20. A column of claim 15 wherein in the solid phase bonded silica product n is 3, X is —S—, each R is hydrogen, p is 1, R$^1$ is hydrogen and R$^2$ is —CH$_3$.

21. A column of claim 15 wherein in the solid phase bonded silica product n is 3, X is —S—, each R is hydrogen, p is zero and R$^2$ is —C$_2$H$_5$.

22. A column of claim 15 wherein in the solid phase bonded silica product n is 3, X is —S—, one R is hydrogen and the other R is —CH$_2$)$_m$COOR$^3$ where m is 1 and R$^3$ is —CH$_3$, p is zero and R$^2$ is —CH$_3$.

23. A column of claim 15 wherein in the solid phase bonded silica product n is 3, X is —O—, one R is hydrogen and the other R is —CH$_3$, p is zero and R$^2$ is —CH$_3$.

24. A column of claim 15 wherein in the solid phase bonded silica product n is 3, X is —O—, each R is —CH$_2$)$_m$COOR$^3$ where m is 1 and R$^3$ is —CH$_3$, p is zero and R$^2$ is —CH$_3$.

25. A column of claim 15 wherein in the solid phase bonded silica product n is 3, X is —S—, each R is hydrogen, p is 1, R$^1$ is —CH$_2$)$_m$COOR$^3$ where m is 1 and R$^3$ is —CH$_3$, and R$^2$ is —CH$_3$.

26. A column of claim 15 wherein in the solid phase bonded silica product n is 3, X is —S—, each R is hydrogen, p is 1, R$^1$ is hydrogen and R$^2$ is —C$_4$H$_9$.

27. A method of preparing a solid phase bonded silica product of the formula:

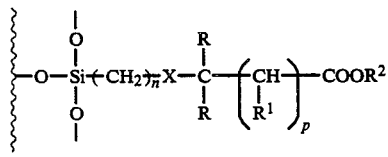

in which

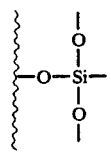

is the backbone of a silica gel or controlled pore glass, X is selected from the group consisting of —O—, —S—,

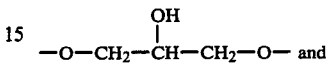

and

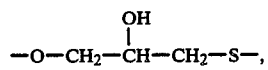

each R and R$^1$ are each independently selected from the group consisting of hydrogen, and alkyl group of from 1 to 3 carbon atoms and —CH$_2$)$_m$COOR$^3$, R$^2$ and R$^3$ are each independently an alkyl group of from 1 to 4 carbon atoms, n is an integer of from 2 to 5, p is zero or one and m is an integer of from 1 to 4, which comprises:

(a) reacting in a suitable inert organic solvent having a boiling point of at least about 80° C.
  (1) a bonded phase silica reactant of the formula

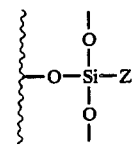

wherein

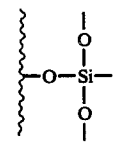

is the backbone of a silica gel or controlled pore glass and Z is selected from the group consisting of

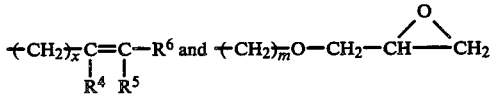

wherein R$^4$, R$^5$ and R$^6$ are each independently selected from the group consisting of hydrogen and an alkyl group of 1 to 3 carbon atoms and x is an integer of from zero to 3 with the proviso that the total number of carbon atoms in the radical Z, when Z is the unsaturated group, does not exceed 5 carbon atoms, and m is an integer of from 2 to 5, with
  (2) a compound of the formula:

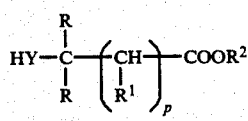

wherein Y is selected from the group consisting of —O— and —S— and each R and $R^1$ are each independently selected from the group consisting of hydrogen, an alkyl group of from 1 to 3 carbon atoms and —$CH_2)_m COOR^3$, and $R^2$ and $R^3$ each independently an alkyl group of from 1 to 4 carbon atoms, p is zero or one and m is an integer of from 1 to 4, (b) recovering the resultant solid fraction from the reaction mixture; and (c) heating said solid fraction at a temperature and for a time sufficient to dry said solid fraction.

28. The method of claim 27 in which the silica is a particulate silica gel having an average particle diameter of from about 20 to about 70 microns and an average pore size of from about 50 to about 500 Angstrom units.

29. A method of preparing a solid phase bonded silica product of the formula:

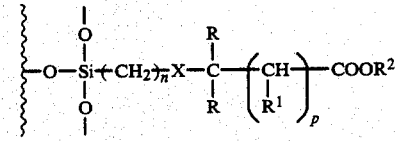

in which

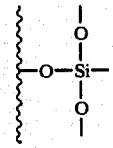

is the backbone of a silica gel or controlled pore glass, X is —S—, each R and $R^1$ are each independently selected from the group consisting of hydrogen, an alkyl group of from 1 to 3 carbon atoms and —$CH_2)_m COOR^3$, $R^2$ and $R^3$ are each independently an alkyl group of from 1 to 4 carbon atoms, n is an integer of from 2 to 5, p is zero or one and m is an integer of from 1 to 4, which comprises:

reacting in the presence of a free radical initiator and a suitable inert organic solvent having a boiling point of at least about 80° C.

(1) a bonded phase silica reactant of the formula:

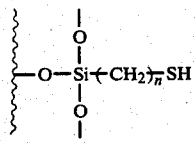

wherein n is an integer of from 2 to 5, with (2) a compound of the formula:

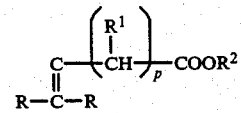

wherein each R and $R^1$ are each independently selected from the group consisting of hydrogen, an alkyl group of from 1 to 3 carbon atoms and —$CH_2)_m COOR^3$, $R^2$ and $R^3$ are each independently of alkyl of from 1 to 4 carbon atoms, n is an integer of from 2 to 5, p is zero or one and m is an integer of from 1 to 4;

(3) recovering the resultant solid fraction from the reaction mixture; and (4) heating the solid fraction at a temperature for a time sufficient to dry said solid fraction.

30. The method of claim 29 in which the silica is a particulate silica gel having an average particle diameter of from about 20 to about 70 microns and an average pore size of from about 50 to about 500 Angstrom units.

* * * * *